US005686411A

United States Patent [19]
Gaeta et al.

[11] Patent Number: 5,686,411
[45] Date of Patent: Nov. 11, 1997

[54] AMYLIN AGONIST PEPTIDES AND USES THEREFOR

[75] Inventors: Laura S. L. Gaeta, Foster City; Howard Jones, Poway; Elisabeth Albrecht, San Diego, all of Calif.

[73] Assignee: Amylin Pharmaceuticals, Inc., San Diego, Calif.

[21] Appl. No.: 447,849

[22] Filed: May 23, 1995

Related U.S. Application Data

[63] Continuation of Ser. No. 794,266, Nov. 19, 1991, abandoned, which is a continuation-in-part of Ser. No. 667,040, Mar. 8, 1991, abandoned.

[51] Int. Cl.$^6$ .......................... A61K 38/16; A61K 38/28; C07K 14/00
[52] U.S. Cl. .................................. 514/12; 514/2; 514/4; 514/866; 530/324
[58] Field of Search ........................ 530/324; 514/2, 514/4, 806, 12

[56] References Cited

U.S. PATENT DOCUMENTS

| 5,124,314 | 6/1992 | Cooper | 514/4 |
| 5,175,145 | 12/1992 | Cooper | 514/4 |
| 5,367,052 | 11/1994 | Cooper et al. | 530/307 |

FOREIGN PATENT DOCUMENTS 0309100  8/1988  European Pat. Off. .

OTHER PUBLICATIONS

Clark, A., et al., *Lancet* ii: 231–234 (1987).
Cooper, G.J.S., et al., *Proc. Natl. Acad. Sci.* (USA) 84:8628–8632 (1987).
Cooper G.J.S., et al., in *Diabetes* 1988, ed. Larkins, R., Zimmet, P. & Chisholm, D. (Elsevier, Amsterdam), pp. 493–496 (1989).
Glenner et al., *Biochem. Biophys. Res Commun.* 155:608–614 (1988).
Westermark et al., *Proc. Natl. Acad. Sci.* (USA) 87: 5036–5040 (1990).
Dayhoff et al., "Atlas of Protein Sequence and Structure", vol. 5 pp. 89–99, 1972.
Goodman & Gilman, "The Pharmacological Basis of Therapeutics" 6th Ed. pp. 1514–1519, 1980.
O'Brien, et al., Islet Amyloid Polypeptide and Insulin Secretion From Isolated Perfused Pancreas of Fed, Fasted, Glucose–Treated, and Dexamethasone–Treated Rats, *Diabetes* 40: 1701–1706 (1991).
Doherty, Endogenous Vasoactive Peptides, *Annual Reports In Medicinal Chemistry* 26: 83–92 (1991).
Ohagi, et al., Sequences of Islet Amyloid Polypeptide Precursors of An Old–World Monkey, The Pig–Tailed Macaque (*Macaca–nemestrina*), and The Dog (*Canis familiaris*), *Diabetologia* 34: 555–558 (1991).
Gustavsson, et al., Normal Transthyretin And Synthetic Transthyretin Fragments Form Amyloid–Like Fibrils In Vitro, *Biochem. Biophys. Res. Commun.* 175: 1159–1164 (1991).
Bell, Molecular Defects In Diabetes–Mellitus, *Diabetes* 40: 413–422 (1991).
Johnson, et al., Newly Identified Pancreatic Protein Islet Amyloid Polypeptide–What Is Its Relationship To Diabetes?, *Diabetes* 40: 310–314 (1991).
Steiner, et al., Is Islet Amyloid Polypeptide A Significant Factor In Pathogenesis Or Pathophysiology of Diabetes?, *Diabetes* 40: 305–309 (1991).
Johnson, et al., Amyloid In The Pancreatic–Islets of The Cougar (*Felis–concolor*) Is Derived From Islet Amyloid Polypeptide (IAPP), *Comp. Biochem. Physiol.* 98: 115–119 (1991).
Porte, Beta Cells In Type II Diabetes Mellitus, *Diabetes* 40: 166–180 (1991).
Stridsberg and Wilander, Islet Amyloid Polypeptide (IAPP)–A Short Review, *Acta Oncologica* 30: 451–456 (1991).
Hilbich, et al., Aggregation and Secondary Structure of Synthetic Amyloid Beta–A4 Peptides of Alzheimer's Disease, *J. Mol. Bio.* 218: 149–163 (1991).

*Primary Examiner*—Cecilia J. Tsang
*Assistant Examiner*—Bennett Celsa
*Attorney, Agent, or Firm*—Lyon & Lyon, L.L.P.

[57] ABSTRACT

Agonist analogues of amylin and related pharmaceutical compositions, and methods of treatment of diabetes and other insulin-requiring states, as well as methods of treatment of hypoglycemia, are provided.

45 Claims, 3 Drawing Sheets

FIGURE 1

$^1$Lys-Cys-Asn-Thr-$^5$Ala-Thr-Cys-Ala-Thr-$^{10}$Gln-Arg-Leu-Ala-Asn-$^{15}$Phe-Leu-Val-His-Ser-$^{20}$Ser-Asn-Asn-Phe-Gly-$^{25}$Ala-Ile-Leu-Ser-Ser-$^{30}$Thr-Asn-Val-Gly-Ser-$^{35}$Asn-Thr-Tyr-NH$_2$

FIGURE 2

Amylin

| | |
|---|---|
| human | KCNTATCATQRLANFLVHSSNNFGAILSSTNVGSNTY-NH$_2$ |
| cat | ----------------IR----L-----P-------- |
| dog | ----------------RT---L-----P-------- |
| rat | ----------------R----L-PV-PP-------- |
| mouse | ----------------R----L-PV-PP-------- |
| hamster | ----------------N--L-PV--P-------- |
| guinea pig | ------------T----R--H-L--A-LP-D------ |

FIGURE 3

$^1A_1$-X-Asn-Thr-$^5$Ala-Thr-Y-Ala-Thr-$^{10}$Gln-Arg-Leu-$B_1$-Asn-$^{15}$Phe-Leu-$C_1$-$D_1$-$E_1$-$^{20}F_1$-$G_1$-Asn-$H_1$-Gly-$^{25}I_1$-$J_1$-Leu-$K_1$-$L_1$-$^{30}$Thr-$M_1$-Val-Gly-Ser-$^{35}$Asn-Thr-Tyr-Z

AMYLIN AGONIST PEPTIDES AND USES THEREFOR

This is a continuation of application Ser. No. 07/794,266 filed on Nov. 19, 1991, now abandoned, which is a continuation-in-part of U.S. application Ser. No. 07/667,040 filed Mar. 8, 1991 (abandoned), which is hereby incorporated by reference.

BACKGROUND

1. Field of the Invention

The field of the invention is medicine, particularly the treatment and prevention of hypoglycemic conditions and other conditions in which enhanced amylin action is of benefit, including insulin-requiring states such as diabetes mellitus. More specifically, the invention relates to the preparation and use of agonist analogues of the peptide hormone amylin.

2. Description of Related Art and Introduction to the Invention

Diabetes mellitus is a serious metabolic disease that is defined by the presence of chronically elevated levels of blood glucose (hyperglycemia). This state of hyperglycemia is the result of a relative or absolute lack of activity of the peptide hormone, insulin. Insulin is produced and secreted by the β cells of the pancreas. Insulin is reported to promote glucose utilization, protein synthesis, and the formation and storage of neutral lipids. Glucose, the principal source of carbohydrate energy, is stored in the body as glycogen, a form of polymerized glucose, which may be converted back into glucose to meet metabolism requirements. Under normal conditions, insulin is secreted at both a basal rate and at enhanced rates following glucose stimulation, all to maintain metabolic homeostasis by the conversion of glucose into glycogen.

The term diabetes mellitus encompasses several different hyperglycemic states. These states include Type 1 (insulin-dependent diabetes mellitus or IDDM) and Type 2 (non-insulin-dependent diabetes mellitus or NIDDM) diabetes. The hyperglycemia present in individuals with Type I diabetes is associated with deficient, reduced, or nonexistent levels of insulin which are insufficient to maintain blood glucose levels within the physiological range. Treatment of Type 1 diabetes involves administration of replacement doses of insulin, generally by the parenteral route. The hyperglycemia present in individuals with Type II diabetes is initially associated with normal or elevated levels of insulin; however, these individuals are unable to maintain metabolic homeostasis due to a state of insulin resistance in peripheral tissues and liver and, as the disease advances, due to a progressive deterioration of the pancreatic β cells which are responsible for the secretion of insulin. Thus, initial therapy of Type 2 diabetes may be based on diet and lifestyle changes augmented by therapy with oral hypoglycemic agents such as sulfonylureas. Insulin therapy is often required, however, especially in the latter stages of the disease, in attempting to produce some control of hyperglycemia and minimize complications of the disease. Thus, many Type 2 diabetics ultimately require insulin in order to survive.

Amyloid is the name given to extracellular deposits of β sheet protein filaments. Deposits of amyloid material have been reported to be found in pancreas of patients with Type 2 diabetes mellitus. Other studies have indicated that the degree of amyloid depositions increases with the degree of hyperglycemia in humans and the severity of Type 2 diabetes. Chemical analysis of pancreatic amyloid led to the surprising and unexpected discovery of the peptide hormone, amylin. Clark, A., et al., *Lancet* ii: 231–234 (1987). This peptide was discovered to be comprised of 37 amino acids, none of which are acidic residues, to have a disulfide linkage between the cysteine residues at positions 2 and 7, and to be C-terminally amidated. Amylin is the major protein constituent of the amyloid which is reported to be found in the pancreatic Islets of Langerhans in patients with type 2 diabetes mellitus.

It has been reported that the presence of both the intramolecular cystine bridge and the carboxy terminal amide group in the peptide structure of the synthetic molecule yield the greatest biological activity to inhibit glycogen synthesis in skeletal muscle. E.g., Cooper, G. J. S., et al., *Proc. Natl. Acad. Sci.* (U.S.A.) 84:8628–8632 (1987); Cooper G. J. S., et al., in *Diabetes* 1988, ed. Larkins, R., Zimmet, P. & Chisholm, D. (Elsevier, Amsterdam), pp. 493–496 (1989). The amino acid sequence of amylin (see FIG. 1) has 46% homology with human calcitonin gene related peptide 2 (CGRP-2).

One report states that a limited segment of the amylin molecule, residues 20–29, is a potential contributor toward amyloid fibril formation in the islets of Langerhans in Type 2 diabetes mellitus. Glenner et al., *Biochem. Biophys. Res Commun.* 155:608–614 (1988). It has also been reported that amino acid sequence differences between amylins from certain mammalian species occur in this region, and further investigation has focused on identifying residues linked to amyloid formation. Westermark et al., *Proc. Natl. Acad. Sci.* (USA) 87: 5036–5040 (1990). The study of Westermark et al. reported attempts to synthesize various 20–29 amino acid segments of amylin sequences from different species followed by a comparison of their ability to form amyloid fibrils. It was proposed that the residues 25–29 of human amylin were the most strongly amyloidogenic and that the proline-for-serine substitution in position 28, as in several rodent species, significantly inhibited fibril formation in the studied decapeptides.

Amylin is a complex peptide, and the synthesis of bioactive preparations of amylin is laborious. Amylin has also been found to have limited solubility and limited stability in solution. We have found that rat amylin has a higher solubility and stability in solution than human amylin. This may be due in some measure, although this is not known, to the different aggregation properties of the amylins from different species. Only the human, non-human primate, and cat species of amylin have been reported to aggregate to form islet amyloid in vivo. The sequences of amylin now reported to have been isolated from a number of species are set forth in FIG. 2.

In Type I diabetes, amylin levels are severely reduced or are nonexistent when compared to normal controls. In the disease state of Type I diabetes mellitus, the β-cells, which are the producers of insulin and amylin, have been destroyed by an autoimmune process. Amylin has been proposed to be useful in the treatment of diabetes mellitus and hypoglycemia, including insulin-induced hypoglycemia. It has also been proposed that the co-administration of insulin with amylin is a superior therapy to the existing administration of insulin alone, and that coadministration of amylin with glucagon for the treatment of hypoglycemia is a superior therapy to the existing administration of glucagon alone. It would be useful to provide, for such purposes and others, less complicated compounds that have the activities of native human amylin, as well as compounds which may show enhanced solubility and/or stability over native human amylin. Such compounds are described and claimed herein.

SUMMARY OF THE INVENTION

The present invention is directed to novel analogues of the peptide hormone amylin. These compounds mimic the effects of amylin, and are referred to as amylin agonists or as agonist analogues of amylin.

The invention is also directed to pharmaceutical compositions comprising the agonist analogues of the present invention, and to methods of treatment and prevention of hypoglycemic conditions and other conditions in which enhanced amylin action is of benefit, including insulin-requiring states such as diabetes mellitus, comprising administering an agonist analogue of amylin to an animal (alone or in conjunction with an insulin or a glucagon).

Definitions

As used herein, the following terms have the following meanings unless expressly stated to the contrary:

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "aryl" refers to carbocyclic aromatic groups of 6 to 14 carbon atoms such as phenyl and naphthyl, as well as heterocyclic aromatic groups containing 1 to 3 heteroatoms (nitrogen, oxygen, sulfur, etc.) such as pyridyl, triazolopyrazine, pyrimidine and the like.

The term "aralkyl" refers to an "aryl" group of 6 to 10 carbon atoms directly attached to an "alkyl" group of 1 to 4 carbon atoms and includes for example benzyl, p-chlorobenzyl, p-methylbenzyl, and 2-phenylethyl.

The term "cycloalkyl" refers to cyclic alkyl groups of 5 to 8 carbon atoms.

BRIEF DESCRIPTION OF THE DRAWINGS

FIG. 1 depicts the amino acid sequence of human amylin.

FIG. 2 depicts a comparison of amino acid sequences of amylins isolated from several mammals.

FIG. 3 depicts the amino acid sequence of novel amylin agonist peptides.

DETAILED DESCRIPTION OF THE INVENTION

According to the present invention, novel agonist analogues of amylin are provided. These analogues are useful as agonists of amylin, including as hyperglycemics, and may be represented by FIG. 3.

In one aspect, the present invention is directed to agonist analogues of FIG. 3, wherein $A_1$ is hydrogen Lys, Ser, Ala, des-α-amino Lys, or acetylated Lys; $B_1$ is Ala, Ser or Thr; $C_1$ is Val, Leu or Ile; $D_1$ is His or Arg; $E_1$ is Ser or Thr; $F_1$ is Ser, Thr, Gln or Asn; $G_1$ is Asn, Gln or His; $H_1$ is Phe, Leu or Tyr; $I_1$ is Ala or Pro; $J_1$ is Ile, Val, Ala or Leu; $K_1$ is Ser, Pro, Leu, Ile or Thr; $L_1$ is Ser, Pro or Thr; $M_1$ is Asn, Asp or Gln; X and Y are independently selected residues having side chains which are chemically bonded to each other to form an intramolecular linkage; and Z is hydroxy, amino, alkylamino, dialkylamino, cycloalkylamino, arylamino, aralkylamino, alkyloxy, aryloxy or aralkyloxy; provided that (a) when $A_1$ is Lys, $B_1$ is Ala, $C_1$ is Val, $D_1$ is His, $E_1$ is Ser, $F_1$ is Ser, $G_1$ is Asn, $H_1$ is Phe, $I_1$ is Ala, $J_1$ is Ile, $K_1$ is Ser, $L_1$ is Ser, and $M_1$ is Asn; (b) when $A_1$ is Lys, $B_1$ is Ala, $C_1$ is Ile, $D_1$ is Arg, $E_1$ is Ser, $F_1$ is Ser, $G_1$ is Asn, $H_1$ is Leu, $I_1$ is Ala, $J_1$ is Ile, $K_1$ is Ser, $L_1$ is Pro, and $M_1$ is Asn; (c) when $A_1$ is Lys, $B_1$ is Ala, $C_1$ is Val, $D_1$ is Arg, $E_1$ is Thr, $F_1$ is Ser, $G_1$ is Asn, $H_1$ is Leu, $I_1$ is Ala, $J_1$ is Ile, $K_1$ is Ser, $L_1$ is Pro, and $M_1$ is Asn; (d) when $A_1$ is Lys, $B_1$ is Ala, $C_1$ is Val, $D_1$ is Arg, $E_1$ is Ser, $F_1$ is Ser, $G_1$ is Asn, $H_1$ is Leu, $I_1$ is Pro, $J_1$ is Val, $K_1$ is Pro, $L_1$ is Pro, and $M_1$ is Asn; (e) when $A_1$ is Lys, $B_1$ is Ala, $C_1$ is Val, $D_1$ is His, $E_1$ is Ser, $F_1$ is Asn, $G_1$ is Asn, $H_1$ is Leu, $I_1$ is Pro, $J_1$ is Val, $K_1$ is Ser, $L_1$ is Pro and $M_1$ is Asn; or (f) when $A_1$ is Lys, $B_1$ is Thr, $C_1$ is Val, $D_1$ is Arg, $E_1$ is Ser, $F_1$ is Ser, $G_1$ is His, $H_1$ is Leu, $I_1$ is Ala, $J_1$ is Ala, $K_1$ is Leu, $L_1$ is Pro and $M_1$ is Asp; then one or more of any of $A_1$ to $M_1$ is not an L-amino acid and Z is not amino.

Suitable side chains for X and Y include groups derived from alkyl sulfhydryls which may form disulfide bonds; alkyl acids and alkyl amines which may form cyclic lactams; alkyl aldehydes or alkyl halides and alkylamines which may condense and be reduced to form an alkyl amine bridge; or side chains which may be connected to form an alkyl, alkenyl, alkynyl, ether or thioether bond. Preferred alkyl chains include lower alkyl groups having from about 1 to about 6 carbon atoms.

An additional aspect of the present invention is directed to agonist analogues of FIG. 3 which are not bridged, and wherein X and Y are independently selected from Ala, Ser, Cys, Val, Leu and Ile or alkyl, aryl, or aralkyl esters and ethers of Ser or Cys.

Biologically active derivatives of the above FIG. 3 agonist analogues are also included within the scope of this invention in which the stereochemistry of individual amino acids may be inverted from (L)/S to (D)/R at one or more specific sites.

Also included within the scope of this invention are the agonist analogues modified by glycosylation of Asn, Ser and/or Thr residues.

Biologically active agonist analogues of amylin are included within the scope of this invention which contain less peptide character. Such peptide mimetics may include, for example, one or more of the following substitutions for —CO—NH— amide bonds: depsipeptides (—CO—O—), iminomethylenes (—CH$_2$—NH—), trans-alkenes (—CH=CH—), β-enaminonitriles (—C(=CH—CN)—NH—), thioamides (—CS—NH—), thiomethylenes (—S—CH$_2$— or —CH$_2$—S—), methylenes (—CH$_2$—C$_2$—) and retro-amides (—NH—CO—).

Compounds of this invention form salts with various inorganic and organic acids and bases. Such salts include salts prepared with organic and inorganic acids, for example, HCl, HBr, H$_2$SO$_4$, H$_3$PO$_4$, trifluoroacetic acid, acetic acid, formic acid, methanesulfonic acid, toluenesulfonic acid, maleic acid, fumaric acid and camphorsulfonic acid. Salts prepared with bases include, for example, ammonium salts, alkali metal salts (such as sodium and potassium salts) and alkali earth salts (such as calcium and magnesium salts). Acetate, hydrochloride, and trifluoroacetate salts are preferred.

The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

The compounds of the invention include various stereoisomers. In the preferred compounds of this invention, the chiral centers on the peptide backbone are all S.

Compounds of the present invention may be prepared by using certain conventional coupling reactions known in the peptide art. The analogues of this invention are prepared by successively adding the desired amino acid to a growing peptide chain. Typically, an α-N-carbamoyl protected amino acid and an amino acid attached to the growing peptide chain on a resin support are reacted at room temperature in an inert solvent such as N-methylpyrrolidone, dimethylformamide or methylene chloride in the presence of coupling agents such as dicyclohexylcarbodiimide 1-hydroxybenzotriazole in the presence of a base such as diisopropylethylamine. The α-N-carbamoyl protecting group is removed from the resultant peptide with a reagent such as trifluoroacetic acid or piperidine, and the coupling reaction repeated with the next desired N-protected amino acid. Suitable N-protecting groups are known in the art, with t-butyloxycarbonyl herein preferred.

Certain preferred methods for synthesis are described in the commonly-assigned copending and commonly assigned patent application Ser. No. 667,040 ("Synthetic Preparation of Amylin and Amylin Analogs", filed Mar. 8, 1991). These methods provide for solid phase synthesis of a peptide which comprises amylin or an amylin analog which has enhanced biological activity and is substantially free of deletion and other contaminating peptides wherein said peptide is synthesized using successive synthesis cycles, whereby in each such synthesis cycle, a designated amino acid is added to a growing peptide chain attached to an insoluble resin support by formation of a peptide linkage between an α-amino group of the growing peptide chain and on α-carboxyl of the designated amino acid; and wherein each synthesis cycle comprises: (a) treating the growing peptide chain under α-amino deprotecting conditions to remove an α-amino group; (b) activating the α-carboxyl group of the α-amino protected designated amino acid; (c) contacting the growing peptide chain and the designated amino acid under coupling conditions to form a peptide linkage between the free α-amino for the peptide chain and the activated α-carboxyl of the designated amino acid; and (d) repeating steps (b) and (c) if the coupling efficiency of step (c) is less than about 97%. It is preferred to repeat steps (b) and (c) if the coupling efficiency is less than about 99%. In another preferred aspect, steps (b) and (c) are repeated in each synthesis cycle. Optionally, the coupling efficiency is measured after each coupling step.

Suitable coupling conditions include use of a solvent system which maximizes swelling of the solid support, minimizes secondary structure elements of the peptide chain during synthesis cycles, and minimizes intrapeptide and interpeptide hydrogen bonding. Preferably the synthesis cycle includes a capping step after the coupling step(s) wherein unreacted α-amino groups of the peptide chain are rendered unreactive. The synthesis cycle is successively repeated using appropriate protected α-amino acids to give amylin or an amylin analog of specified sequence. After completions of the successive synthesis cycles, said amylin or amylin analog is cleaved from the solid support. It is preferred that the cysteine residues of the peptide chain are selectively deprotected and an intramolecular disulfide bond is formed before cleaving the peptide bond from the solid support.

Suitable α-amino protective groups include t-butoxycarbonyl and 9-fluorenylmethoxycarbonyl. In one preferred aspect, when t-butoxycarbonyl is used as the α-amino protecting group, the α-carboxyl groups are activated using dicyclohexylcarbodiimide and 1-hydroxybenzotriazole to form 1-hydroxybenzotriazole esters. A particularly preferred solvent system comprise N-methylpyrrolidone.

The preparation of certain agonist analogues of amylin within the invention is described in Examples 1 to 17 herein. In addition, other agonist analogues which may be prepared according to the above procedures are set forth in Table II herein. The compounds of the invention may also be prepared using recombinant DNA techniques, using methods now known in the art. See, e.g., Sambrook et al., *Molecular Cloning: A Laboratory Manual*, 2d Ed., Cold Spring Harbor (1989).

The nomenclature of the compounds of the present invention can be used to indicate both the peptide that the sequence is based on and the modifications made to any basic peptide amylin sequence, such as human amylin. An amino acid preceded by a superscript number indicates that the named amino acid replaces the amino acid normally present at the amino acid position of the superscript in the basic amino acid sequence. For example, "$^{18}$Arg$^{25,28}$Pro-h-amylin" refers to a peptide based on the sequence of "h-amylin" or "human-amylin" having the following substitutions: Arg replacing His at residue 18, Pro replacing Ala at residue 25 and Pro replacing Ser at residue 28. The term "des-$^{1}$Lys-h-amylin" refers to a peptide based on the sequence of human amylin, with the first, or N-terminal, amino acid deleted.

The agonist analogues of amylin of this invention are useful in view of their pharmacological properties. In particular, compounds of this invention possess activity as amylin agonist agents, as will be evidenced by activity in the receptor binding assay and the soleus muscle assay described in Examples 18 and 19, respectively. Amylin agonist activity of compounds may also be assessed by the ability to induce hyperlactemia and/or hyperglycemia in mammals. In addition to the description of compounds pursuant to FIG. 3, certain preferred compounds are set forth in Table I. The preferred compounds des-$^{1}$Lys-h-amylin, $^{28}$Pro-h-amylin, $^{25,28,29}$Pro-h-amylin, $^{18}$Arg$^{25,28}$Pro-h-amylin, and des-$^{1}$Lys$^{18}$Arg$^{25,28}$Pro-h-amylin, all show amylin activity in vivo in treated test animals, provoking marked hyperlactemia followed by hyperglycemia. In addition to having activities characteristic of amylin, certain of the preferred compounds of the invention have also been found to possess more desireable solubility and stability characteristics when compared to human amylin. These preferred compounds include $^{25}$Pro$^{26}$Val$^{28,29}$Pro-h-amylin, $^{25,28,29}$Pro-h-amylin, and $^{18}$Arg$^{25,28}$Pro-h-amylin.

Compounds described herein which are especially preferred include $^{18}$Arg$^{25,28}$Pro-h-amylin, des-$^{1}$Lys$^{18}$Arg$^{25,28}$Pro-h-amylin, $^{18}$Arg$^{25,28,29}$Pro-h-amylin, des-$^{1}$Lys$^{18}$Arg$^{25,28,29}$Pro-h-amylin, $^{25,28,29}$Pro-h-amylin, des-$^{1}$Lys$^{25,28,29}$Pro-h-amylin, and $^{25}$Pro$^{26}$Val$^{28,29}$Pro-h-amylin. Still further amylin agonist peptide compounds are listed in Table II. They include:

$^{23}$Leu$^{25}$Pro$^{26}$Val$^{28,29}$Pro-h-amylin;

$^{23}$Leu$^{25}$Pro$^{26}$Val$^{28}$Pro-h-amylin;

des-$^{1}$Lys$^{23}$Leu$^{25}$Pro$^{26}$Val$^{28}$Pro-h-amylin;

$^{18}$Arg$^{23}$Leu$^{25}$Pro$^{26}$Val$^{28}$Pro-h-amylin;

$^{18}$Arg$^{23}$Leu$^{25,28,29}$Pro-h-amylin;

$^{18}$Arg$^{23}$Leu$^{25,28}$Pro-h-amylin;

$^{17}$Ile$^{23}$Leu$^{25,28,29}$Pro-h-amylin;

$^{17}$Ile$^{25,28,29}$Pro-h-amylin;

des-$^{1}$Lys$^{17}$Ile$^{23}$Leu$^{25,28,29}$Pro-h-amylin;

$^{17}$Ile$^{18}$Arg$^{23}$Leu-h-amylin;

$^{17}$Ile$^{18}$Arg$^{23}$Leu$^{26}$Val$^{29}$Pro-h-amylin;

$^{17}$Ile$^{18}$Arg$^{23}$Leu$^{25}$Pro$^{26}$Val$^{28,29}$Pro-h-amylin;

$^{13}$Thr$^{21}$His$^{23}$Leu$^{26}$Ala$^{28}$Leu$^{29}$Pro-$^{31}$Asp-h-amylin;

$^{13}$Thr$^{21}$His$^{23}$Leu$^{26}$Ala$^{29}$Pro$^{31}$Asp-h-amylin;

des-$^{1}$Lys$^{13}$Thr$^{21}$His$^{23}$Leu$^{26}$Ala$^{28}$Pro$^{31}$Asp-h-amylin;

$^{13}$Thr$^{18}$Arg$^{21}$His$^{23}$Leu$^{26}$Ala$^{29}$Pro$^{31}$Asp-h-amylin;

$^{13}$Thr$^{18}$Arg$^{21}$His$^{23}$Leu$^{28,29}$Pro$^{31}$Asp-h-amylin; and, $^{13}$Thr$^{18}$Arg$^{21}$His$^{23}$Leu$^{25}$Pro$^{26}$Ala$^{28,29}$Pro$^{31}$Asp-h-amylin.

The compounds of this invention can be combined with pharmaceutical carriers to prepare pharmaceutical forms suitable for parenteral administration. Experimental responses of the compounds support the clinical application of such pharmaceutical compositions in the treatment of diabetes mellitus and other insulin-requiring states, as well as in the prevention and treatment of episodes of hypoglycemia. The compounds of this invention can also be combined with insulin for the treatment of diabetes mellitus and other insulin-requiring states. By "insulin" is meant a polypeptide or its equivalent useful in regulation of blood glucose levels. A general description of such insulins is provided in Goodman and Gilman's The Pharmacological Basis of Therapeutics, 8th Ed., Pergamon Press (1990). Such insulins can be fast acting, intermediate acting, or long acting. Various derivatives of insulin exist and are useful in this invention. See, e.g., U.S. Pat. Nos. 5,049,547, 5,028, 587, and 5,016,643. Insulin peptides are also useful (see, e.g., U.S. Pat. No. 5,008,241), as are analogues (see, e.g., U.S. Pat. Nos. 4,992,417 and 4,992,418). Such compositions can be administered by any standard route, including nasal administration (see, e.g., U.S. Pat. Nos. 4,988,512 and 4,985,242, and 2 BioWorld Today, No. 125 (1991)). The compounds of this invention are also useful in combination with a glucagon for the prevention and treatment of hypoglycemia. See Young et al., U.S. application Ser. No. 07/640,478, filed Jan. 10, 1991, entitled "Hyperglycemic Compositions," which is incorporated herein by reference.

Compositions or products of the invention may conveniently be provided in the form of solutions suitable for parenteral (including intravenous, intramuscular and subcutaneous) or nasal or oral administration. In many cases, it will be convenient to provide an agonist analogue of amylin and an insulin or glucagon in a single composition or solution for administration together. In other cases, it may be more advantageous to administer an insulin or a glucagon separately from said agonist analogue. A suitable administration format may best be determined by a medical practitioner for each patient individually. Suitable pharmaceutically acceptable carriers and their formulation are described in standard formulation treatises, e.g., Remington's Pharmaceutical Sciences by E. W. Martin. See also Wang, Y. J. and Hanson, M. A. "Parenteral Formulations of Proteins and Peptides: Stability and Stabilizers," Journal of Parenteral Science and Technology, Technical Report No. 10, Supp. 42:2S (1988). Suitable formulations including insulin or glucagon are known in the art.

The agonist preparations of the invention may be stabilized at neutral pH. Since the products of the invention are amphoteric they may be utilized as free bases, as acid addition salts or as metal salts. The salts must, of course, be pharmaceutically acceptable, and these will include metal salts, particularly alkali and alkaline earth metal salts, e.g., potassium or sodium salts. A wide variety of pharmaceutically acceptable acid addition salts are available, as described above. These include those prepared from both organic and inorganic acids, preferably mineral acids. Typical acids which may be mentioned by way of example include citric, succinic, lactic, hydrochloric and hydrobromic acids. Such products are readily prepared by procedures well known to those skilled in the art.

The products of the invention will normally be provided as parenteral compositions for injection or infusion. They can, for example, be suspended in an inert oil, suitably a vegetable oil such as sesame, peanut, or olive oil. Alternatively, they can be suspended in an aqueous isotonic buffer solution at a pH of about 5.6 to 7.4. Useful buffers include sodium citrate-citric acid and sodium phosphate-phosphoric acid. A form of repository or "depot" slow release preparation may be used so that therapeutically effective amounts of the preparation are delivered into the bloodstream over many hours or days following transdermal injection.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

The therapeutically useful compositions of the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of an agonist compound with or without insulin or glucagon which will be effective in one or multiple doses to control or reestablish blood sugar at the selected level. Therapeutically effective amounts of an agonist analogue of amylin as described herein for the treatment of hypoglycemia are those that increase blood sugar levels, preferably to above 80 mg/dl. Therapeutically effective amounts of such agonist analogues for the treatment of diabetes mellitus and other insulin-requiring states are those sufficient to provide for reduced incidence of insulin overdose or undesired hypoglycemia. As will be recognized by those in the field, an effective amount of therapeutic agent will vary with many factors including the age and weight of the patient, the patient's physical condition, the blood sugar level to be obtained, and other factors. Typical dosage units for treatment of diabetes mellitus will contain from about 0.1 to 5 mg of an amylin agonist compound and, if desired, about 0.5 to about 10 mg of an insulin. Typical dosage units for the treatment of hypoglycemia will contain about 0.5 to 1.0 mg of an amylin agonist compound and, if desired, the art recognized quantity, or less, of a glucagon.

As set forth above, compositions useful in the invention are formulated by standard procedure. These compositions are also administered by standard procedure. Suitable doses are readily determined by those in the art, examples of which are provided above.

To assist in understanding the present invention, the following examples are included which describe the results of a series of experiments. The following examples relating to this invention should not, of course, be construed as specifically limiting the invention. Such variations of the invention, now known or later developed, which would be within the purview of one skilled in the art are considered to fall within the scope of the present invention as hereinafter claimed.

EXAMPLES

Example 1

Preparation of $^{28}$Pro-human-Amylin

Solid phase synthesis of this analogue of human ("h-") amylin using methylbenzhydrylamine anchor-bond resin and $N^\alpha$-Boc/benzyl-side chain protection was carried out by standard peptide synthesis methods. The $^{2,7}$-[disulfide] amylin-MBHA-resin was obtained by treatment of Acm-protected cysteines with thallium (III) trifluoroacetate in trifluoroacetic acid. After cyclization was achieved the resin and side chain protecting groups were cleaved with liquid hydrofluoric acid ("HF") in the presence of dimethylsulfide and anisole. The $^{28}$Pro-h-amylin was purified by preparative HPLC. The peptide was found to be homogeneous by analytical HPLC and capillary electrophoresis and the structure confirmed by amino acid analysis and sequence analysis. The product gave the desired mass ion. FAB mass spec: (M+1)/e=3914.

Example 2

Preparation of $^{25}$Pro$^{26}$Val$^{28,29}$Pro-h-Amylin

Solid phase synthesis of this amylin analogue using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment with thallium (III) trifluoroacetate in trifluoroacetic acid. After cyclization was achieved the resin and side chain protecting groups were cleaved with liquid HF in the presence of dimethylsulfide and anisole. The $^{25}$Pro$^{26}$Val$^{28,29}$Pro-h-amylin was purified by preparative HPLC. The peptide was found to be homogeneous by analytical HPLC and capillary electrophoresis and the structure confirmed by amino acid analysis and sequence analysis. The product gave the desired mass ion. FAB mass spec: (M+1)/e=3936.

Example 3

Preparation of $^{2,7}$Cyclo-[$^2$Asp,$^7$Lys]-h-Amylin

Solid phase synthesis of this amylin analogue using methylbenzhydrylamine anchor-bond resin and $N^\alpha$-Boc/benzyl-side chain protection was carried out by standard peptide synthesis methods. $^2$Asp and $^7$Lys were introduced with Boc-$^2$Asp(Fmoc)-OH and Boc-$^7$Lys(Fmoc)-OH. Following selective side-chain deprotection with piperidine the side-chain to side-chain ($^2$Asp-$^7$Lys) cyclization was carried out using benzotriazol-1yl-oxy-tris(dimethylamino)-phosphonium hexafluorophosphate (BOP reagent). Cyclization was as described in Di Maio, J., et al,. *J. Med. Chem.* 33:661–667 (1990); Felix, A. M., et al., *Int J. Pept. Prot. Res.* 32:441 (1988). The $^{2,7}$cyclo-[$^2$Asp,$^7$Lys]amylin-MBHA-resin obtained after cyclization was cleaved with liquid HF in the presence of dimethylsulfide and anisole. The $^{2,7}$cyclo-[$^2$Asp,$^7$Lys]-h-amylin was purified by preparative HPLC. The peptide was found to be homogeneous by analytical HPLC and capillary electrophoresis and the structure confirmed by amino acid analysis and sequence analysis. FAB mass spec: (M+1)/e=3925.

Example 4

Preparation of des-$^1$Lys-h-Amylin

Solid phase synthesis of des-$^1$Lys-h-amylin (also represented as $^{2-37}$h-amylin) using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The des-$^1$Lys-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: (M+H)$^+$=3,775.

Example 5

Preparation of $^1$Ala-h-Amylin

Solid phase synthesis of $^1$Ala-h-amylin using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^1$Ala-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: (M+H)$^+$=3,847.

Example 6

Preparation of $^1$Ser-h-Amylin

Solid phase synthesis of $^1$Ser-h-amylin using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cystsines with thallium (III) trifluoroacetate in trifluoroacetic acid. After cyclization was achieved the resin and side chain protecting groups were cleaved with liquid HF in the presence of dimethylsulfide and anisole. The $^1$Ser-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: (M+H)$^+$=3,863.

Example 7

Preparation of $^{29}$Pro-h-Amylin

Solid phase synthesis of this analogue of human amylin using methylbenzhydrylamine anchor-bond resin and $N^\alpha$-Boc/benzyl-side chain protection was carried out by standard peptide synthesis methods. The $^{2,7}$-[disulfide] amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{29}$Pro-h-amylin was purified by preparative HPLC. The peptide was found to be homogeneous by analytical HPLC and capillary electrophoresis and the structure confirmed by amino acid analysis and sequence analysis. The product gave the desired mass ion. FAB mass spec: $(M+H)^+ = 3916$.

Example 8

Preparation of $^{25,28}$Pro-h-Amylin

Solid phase synthesis of $^{25,28}$Pro-h-amylin using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{25,28}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+ = 3,939$.

Example 9

Preparation of des-$^1$Lys$^{25,28}$Pro-h-Amylin

Solid phase synthesis of des-$^1$Lys$^{25,28}$Pro-h-amylin using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The des-$^1$Lys$^{25,28}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+ = 3,811$.

Example 10

Preparation of $^{18}$Arg$^{25,28}$Pro-h-Amylin

Solid phase synthesis of $^{18}$Arg$^{25,28}$Pro-h-amylin using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{18}$Arg$^{25,28}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+ = 3,959$.

Example 11

Preparation of des-$^1$Lys$^{18}$Arg$^{25,28}$Pro-h-Amylin

Solid phase synthesis of des-$^1$Lys$^{18}$Arg$^{25,28}$Pro-h-amylin using methylbenzhydrylamine anchor-bond resin and $N^\alpha$-Boc/benzyl-side chain protection was carried out by standard peptide synthesis methods. The $^{2,7}$-[disulfide] amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The des-$^1$Lys$^{18}$Arg$^{25,28}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+ = 3,832$.

Example 12

Preparation of $^{18}$Arg$^{25,28,29}$pro-h-Amylin

Solid phase synthesis of $^{18}$Arg$^{25,28,29}$Pro-h-amylin using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{18}$Arg$^{25,28,29}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+ = 3,971$.

Example 13

Preparation of des-$^1$Lys$^{18}$Arg$^{25,28,29}$Pro-h-Amylin

Solid phase synthesis of des-$^1$Lys$^{18}$Arg$^{25,28,29}$Pro-h-amylin using methylbenzhydrylamine anchor-bond resin and $N^\alpha$-Boc/benzyl-side chain protection was carried out by standard peptide synthesis methods. The $^{2,7}$-[disulfide] amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The des-$^1$Lys$^{18}$Arg$^{25,28,29}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+ = 3,843$.

Example 14

Preparation of $^{25,28,29}$Pro-h-Amylin

Solid phase synthesis of $^{25,28,29}$Pro-h-amylin using methylbenzhydrylamine anchor-bond resin and $N^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The $^{25,28,29}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+=3,949$.

Example 15

Preparation of des-$^1$Lys$^{25,28,29}$Pro-h-Amylin

Solid phase synthesis of des-$^1$Lys$^{25,28,29}$Pro-h-amylin using methylbenzhydrylamine anchor-bond resin and N$^\alpha$-Boc/benzyl-side chain protection was carried out by standard peptide synthesis methods. The $^{2,7}$-[disulfide]amylin-MBHA-resin was obtained by treatment of Acm-protected cysteines with thallium (III) trifluoroacetate in trifluoroacetic acid. After cyclization was achieved the resin and side chain protecting groups were cleaved with liquid HF in the presence of dimethylsulfide and anisole. The des-$^1$Lys$^{25,28,29}$Pro-h-amylin was purified by preparative reversed-phase HPLC. The peptide was found to be homogeneous by analytical HPLC and capillary electrophoresis and the structure confirmed by amino acid analysis and sequence analysis. The product gave the desired mass ion. FAB mass spec: $(M+H)^+=3,823$.

Example 16

Preparation of des-$^1$Lys$^{25}$Pro$^{26}$Val$^{28,29}$-Pro-h-Amylin

Solid phase synthesis of this h-amylin analogue using methylbenzhydrylamine anchor-bond resin and N$^\alpha$-Boc/benzyl-side chain protection is carried out by standard peptide synthesis methods, and the $^{2,7}$-[disulfide]amylin-MBHA-resin obtained by treatment with thallium (III) trifluoroacetate in trifluoroacetic acid. After cyclization is achieved the resin and side chain protecting groups are cleaved with liquid HF in the presence of dimethylsulfide and anisole. The des-$^1$Lys$^{25}$Pro$^{26}$Val$^{28,29}$Pro-h-amylin is then purified by preparative HPLC.

Example 17

Preparation of [(D)-$^{11}$Arg]-Amylin

Solid phase synthesis of this amylin analogue using methylbenzhydrylamine anchor-bond resin and N$^\alpha$-Boc/benzyl-side chain protection is carried out by standard peptide synthesis methods. (D)-$^{11}$Arg is introduced with Boc-(D)-$^{11}$Arg(Mtr)-OH. The $^{2,7}$-[disulfide]amylin-MBHA-resin, obtained by treatment with thallium (III) trifluoroacetate in trifluoroacetic acid, is cyclized and the resin and side chain protecting groups are cleaved with liquid HF in the presence of dimethylsulfide and anisole. The [(D)-$^{11}$Arg]-amylin is then purified by preparative HPLC.

Example 18

Receptor Binding Assay

Evaluation of the binding of compounds of the invention to amylin receptors was carried out as follows. $^{125}$I-rat amylin (Bolton-Hunter labeled at the N-terminal lysine) was purchased from Amersham Corporation (Arlington Heights, Ill.). Specific activities at time of use ranged from 1950 to 2000 Ci/mmol. Unlabeled peptides were obtained from BACHEM Inc. (Torrance, Calif.) and Peninsula Laboratories (Belmont, Calif.).

Male Sprague-Dawley rats (200–250) grams were sacrificed by decapitation. Brains were removed to cold phosphate-buffered saline (PBS). From the ventral surface, cuts were made rostral to the hypothalamus, bounded laterally by the olfactory tracts and extending at a 45° angle medially from these tracts. This basal forebrain tissue, containing the nucleus accumbens and surrounding regions, was weighed and homogenized in ice-cold 20 mM HEPES buffer (20 mM HEPES acid, pH adjusted to 7.4 with NaOH at 23° C.). Membranes were washed three times in fresh buffer by centrifugation for 15 minutes at 48,000×g. The final membrane pellet was resuspended in 20 mM HEPES buffer containing 0.2 mM phenylmethylsulfonyl fluoride (PMSF).

To measure $^{125}$I-amylin binding, membranes from 4 mg original wet weight of tissue were incubated with $^{125}$I-amylin at 12–16 pM in 20 mM HEPES buffer containing 0.5 mg/ml bacitracin, 0.5 mg/ml bovine serum albumin, and 0.2 mM PMSF. Solutions were incubated for 60 minutes at 23° C. Incubations were terminated by filtration through GF/B glass fiber filters (Whatman Inc., Clifton, N.J.) which had been presoaked for 4 hours in 0.3% poylethyleneimine in order to reduce nonspecific binding of radiolabeled peptides. Filters were washed immediately before filtration with 5 ml cold PBS, and immediately after filtration with 15 ml cold PBS. Filters were removed and radioactivity assessed in a gamma-counter at a counting efficiency of 77%. Competition curves were generated by measuring binding in the presence of $10^{-12}$ to $10^{-6}$ M unlabeled test compound and were analyzed by nonlinear regression using a 4-parameter logistic equation (Inplot program; GraphPAD Software, San Diego).

In this assay, purified human amylin binds to its receptor at a measured IC$_{50}$ of about 50 pM. Results for test compounds of the invention are set forth in Table I, showing that each of the compounds has significant receptor binding activity.

Example 19

Soleus Muscle Assay

Evaluation of the amylin agonist activity of compounds of the invention was carried out using the soleus muscle assay as follows. Male Harlan Sprague-Dawley rats of approximately 200 g mass were used in order to maintain mass of the split soleus muscle less than 40 mg. The animals were fasted for 4 hours prior to sacrifice by decapitation. The skin was stripped from the lower limb which was then pinned out on corkboard. The *tendo achilles* was cut just above *os calcis* and *m. gastrocnemius* reflected out from the posterior aspect of the tibia. *M. soleus*, a small 15–20 mm long, 0.5 mm thick flat muscle on the bone surface of *m. gastrocnemius* was then stripped clear and the perimysium cleaned off using fine scissors and forceps. *M. soleus* was then split into equal parts using a blade passed antero-posteriorly through the belly of the muscle to obtain a total of 4 muscle strips from each animal. After dissecting the muscle from the animal, it was kept for a short period in physiological saline. It was not necessary that the muscle be held under tension as this had no demonstrable effects on radioglucose incorporation into glycogen.

Muscles were added to 50 mL Erlenmeyer flasks containing 10 mL of a pregassed Krebs-Ringer bicarbonate buffer containing (each liter) NaCl 118.5 mmol (6.93 g), KCl 5.94 mmol (443 mg), CaCl$_2$ 2.54 mmol (282 mg), MgSO$_4$ 1.19 mmol (143 mg), KH$_2$PO$_4$ 1.19 mmol (162 mg), NaHCO$_3$ 25 mmol (2.1 g), 5.5 mmol glucose (1 g) and recombinant human insulin (Humulin-R, Eli Lilly, Indiana) and the test compound, as detailed below. pH at 37° C. was verified as being between 7.1 and 7.4. Muscles were assigned to different flasks so that the 4 muscle pieces from each animal were evenly distributed among the different assay conditions. The incubation media were gassed by gently blowing carbogen (95% $O_2$, 5% $CO_2$) over the surface while being continuously agitated at 37° C. in an oscillating water bath. After a half-hour "preincubation" period, 0.5 μCi of U-$^{14}$C-glucose was added to each flask which was incubated for a further 60 minutes. Each muscle piece was then rapidly removed, blotted and frozen in liquid $N_2$, weighed and stored for subsequent determination of $^{14}$C-glycogen.

$^{14}$C-glycogen determination was performed in a 7 mL scintillation vial. Each frozen muscle specimen was placed in a vial and digested in 1 mL 60% potassium hydroxide at 70° C. for 45 minutes under continuous agitation. Dissolved glycogen was precipitated out onto the vial by the addition of 3 mL absolute ethanol and overnight cooling at -20° C. The supernatant was gently aspirated, the glycogen washed again with ethanol, aspirated and the precipitate dried under vacuum. All ethanol is evaporated to avoid quenching during scintillation counting. The remaining glycogen was redissolved in 1 mL water and 4 mL scintillation fluid and counted for $^{14}$C.

The rate of glucose incorporation into glycogen (expressed in μmol/g/hr) was obtained from the specific activity of $^{14}$C-glucose in the 5.5 mM glucose of the incubation medium, and the total $^{14}$C counts remaining in the glycogen extracted from each muscle. Dose/response curves were fitted to a 4-parameter logistic model using a least-squares iterative routine (ALLFIT, v2.7, NIH, Maryland) to derive $EC_{50}$'s. Since $EC_{50}$ is log-normally distributed, it is expressed ± standard error of the logarithm. Pairwise comparisons were performed using t-test based routines of SYSTAT (Wilkinson, "SYSTAT: the system for statistics," SYSTAT Inc., Evanston Ill. (1989)).

some commercial preparations which are less than 90% pure have higher $EC_{50}$'s due to the presence of contaminants that result in a lower measured activity. Results for test compounds are set forth in Table I, showing that each of the compounds has amylin activity.

TABLE I

| | Receptor Binding Assay $IC_{50}$ (pM) | Soleus Muscle Assay $EC_{50}$ (nM) |
|---|---|---|
| 1) $^{28}$Pro-h-Amylin | 15.0 | 2.64 |
| 2) $^{25}$Pro$^{26}$Val$^{28,29}$Pro-h-Amylin | 18.0 | 4.68 |
| 3) $^{2,7}$Cyclo-[$^2$Asp,$^7$Lys]-h-Amylin | 310.0 | 6.62 |
| 4) $^{2-37}$h-Amylin | 236.0 | 1.63 |
| 5) $^1$Ala-h-Amylin | 148.0 | 12.78 |
| 6) $^1$Ser-h-Amylin | 33.0 | 8.70 |
| 7) $^{29}$Pro-h-Amylin | 64.0 | 3.78 |
| 8) $^{25,28}$Pro-h-Amylin | 26.0 | 13.20 |
| 9) des-$^1$Lys$^{25,28}$Pro-h-Amylin | 85.0 | 7.70 |
| 10) $^{18}$Arg$^{25,28}$Pro-h-Amylin | 32.0 | 2.83 |
| 11) des-$^1$Lys$^{18}$Arg$^{25,28}$Pro-h-Amylin | 82.0 | 3.77 |
| 12) $^{18}$Arg$^{25,28,29}$Pro-h-Amylin | 21.0 | 1.25 |
| 13) des-$^1$Lys$^{18}$Arg$^{25,28,29}$Pro-h-Amylin | 21.0 | 1.86 |
| 14) $^{25,28,29}$Pro-h-Amylin | 10.0 | 3.71 |
| 15) des-$^1$Lys$^{25,28,29}$Pro-h-Amylin | 14.0 | 4.15 |

TABLE II

| | $A_1$ | $B_1$ | $C_1$ | $D_1$ | $E_1$ | $F_1$ | $G_1$ | $H_1$ | $I_1$ | $J_1$ | $K_1$ | $L_1$ | $M_1$ | Z |
|---|---|---|---|---|---|---|---|---|---|---|---|---|---|---|
| 16) | Lys | Ala | Val | His | Ser | Ser | Asn | Leu | Pro | Val | Pro | Pro | Asn | —$NH_2$ |
| 17) | Lys | Ala | Val | His | Ser | Ser | Asn | Leu | Pro | Val | Pro | Ser | Asn | —$NH_2$ |
| 18) | Hydrogen | Ala | Val | His | Ser | Ser | Asn | Leu | Pro | Val | Pro | Ser | Asn | —$NH_2$ |
| 19) | Lys | Ala | Val | Arg | Ser | Ser | Asn | Leu | Pro | Val | Pro | Ser | Asn | —$NH_2$ |
| 20) | Lys | Ala | Val | Arg | Ser | Ser | Asn | Leu | Pro | Ile | Pro | Pro | Asn | —$NH_2$ |
| 21) | Lys | Ala | Val | Arg | Ser | Ser | Asn | Leu | Pro | Ile | Pro | Ser | Asn | —$NH_2$ |
| 22) | Lys | Ala | Ile | His | Ser | Ser | Asn | Leu | Pro | Ile | Pro | Pro | Asn | —$NH_2$ |
| 23) | Lys | Ala | Ile | His | Ser | Ser | Asn | Phe | Pro | Ile | Pro | Pro | Asn | —$NH_2$ |
| 24) | Hydrogen | Ala | Ile | His | Ser | Ser | Asn | Leu | Pro | Ile | Pro | Pro | Asn | —$NH_2$ |
| 25) | Lys | Ala | Ile | Arg | Ser | Ser | Asn | Leu | Ala | Ile | Ser | Ser | Asn | —$NH_2$ |
| 26) | Lys | Ala | Ile | Arg | Ser | Ser | Asn | Leu | Ala | Val | Ser | Pro | Asn | —$NH_2$ |
| 27) | Lys | Ala | Ile | Arg | Ser | Ser | Asn | Leu | Pro | Val | Pro | Pro | Asn | —$NH_2$ |
| 28) | Lys | Thr | Val | His | Ser | Ser | His | Leu | Ala | Ala | Leu | Pro | Asp | —$NH_2$ |
| 29) | Lys | Thr | Val | His | Ser | Ser | His | Leu | Ala | Ala | Ser | Pro | Asp | —$NH_2$ |
| 30) | Hydrogen | Thr | Val | His | Ser | Ser | His | Leu | Ala | Ala | Pro | Ser | Asp | —$NH_2$ |
| 31) | Lys | Thr | Val | Arg | Ser | Ser | His | Leu | Ala | Ala | Ser | Pro | Asp | —$NH_2$ |
| 32) | Lys | Thr | Val | Arg | Ser | Ser | His | Leu | Ala | Ile | Pro | Pro | Asp | —$NH_2$ |
| 33) | Lys | Thr | Val | Arg | Ser | Ser | His | Leu | Pro | Ala | Pro | Pro | Asp | —$NH_2$ |

Dose response curves were generated with muscles added to media containing 7.1 nM (1000 μU/mL) insulin and each test compound added at final (nominal) concentrations of 0, 1, 3, 10, 30, 100, 300 and 1000 nM. Each assay also contained internal positive controls consisting of a single batch of archived rat amylin, lyophilized and stored at -70° C.

Human amylin is a known hyperglycemic peptide, and $EC_{50}$ measurements of amylin preparations in the soleus muscle assay range typically from about 1–10 nM, although

We claim:

1. An agonist analogue of amylin having the amino acid sequence:

$^1A_1-X-Asn-Thr-^5Ala-Thr-Y-Ala-Thr-^{10}Gln-Arg-Leu-B_1-Asn-^{15}Phe-Leu-C_1-D_1-E_1-^{20}F_1-G_1-Asn-H_1-Gly-^{25}Pro-I_1-Leu-Pro-J_1-^{30}Thr-K_1-Val-Gly-Ser-^{35}Asn-Thr-Tyr-Z$ wherein
  $A_1$ is Lys, Ala, Ser or hydrogen;
  $B_1$ is Ala, Ser or Thr;
  $C_1$ is Val, Leu or Ile;
  $D_1$ is His or Arg;
  $E_1$ is Ser or Thr;
  $F_1$ is Ser, Thr, Gln or Asn;
  $G_1$ is Asn, Gln or His;
  $H_1$ is Phe, Leu or Tyr;
  $I_1$ is Ile, Val, Ala or Leu;
  $J_1$ is Ser, Pro or Thr;
  $K_1$ is Asn, Asp or Gln;
  X and Y are independently selected amino acid residues having side chains which are chemically bonded to each other to form an intramolecular linkage, wherein said intramolecular linkage is a disulfide bond, a lactam or a thioether linkage; and Z is amino, alkylamino, dialkylamino, cycloalkylamino, arylamino, aralkylamino, alkyloxy, aryloxy or aralkyloxy; and provided that when $A_1$ is Lys, $B_1$ is Ala, $C_1$ is Val, $D_1$ is Arg, $E_1$ is Ser, $F_1$ is Ser, $G_1$ is Asn, $H_1$ is Leu, $I_1$ is Val, $J_1$ is Pro, and $K_1$ is Asn; then one or more of $A_1$ to $K_1$ is a D-amino acid and Z is selected from the group consisting of alkylamino, dialkylamino, cycloalkylamino, arylamino, aralkylamino, alkyloxy, aryloxy or aralkyloxy.

2. An agonist analogue of amylin according to claim 1 wherein X and Y are Cys residues linked by a disulfide bond.

3. An agonist analogue of amylin according to claim 2 wherein Z is amino.

4. An agonist analogue of amylin having the amino acid sequence:

$^1A_1-X-Asn-Thr-^5Ala-Thr-Y-Ala-Thr-^{10}Gln-Arg-$
$Leu-B_1-Asn-^{15}Phe-Leu-C_1-D_1-E_1-^{20}F_1-G_1-$
$Asn-H_1-Gly-^{25}Pro-I_1-Leu-J_1-Pro-^{30}Thr-K_1-$
$Val-Gly-Ser-^{35}Asn-Thr-Tyr-Z$ wherein $A_1$ is Lys, Ala, Ser or hydrogen;

$B_1$ is Ala, Ser or Thr;

$C_1$ is Val, Leu or Ile;

$D_1$ is His or Arg;

$E_1$ is Ser or Thr;

$F_1$ is Ser, Thr, Gln or Asn;

$G_1$ is Asn, Gln or His;

$H_1$ is Phe, Leu or Tyr;

$I_1$ is Ile, Val, Ala or Leu;

$J_1$ is Ser, Pro, Leu, Ile or Thr;

$K_1$ is Asn, Asp or Gln;

X and Y are independently selected amino acid residues having side chains which are chemically bonded to each other to form an intramolecular linkage, wherein said intramolecular linkage is a disulfide bond, a lactam or a thioether linkage; and Z is amino, alkylamino, dialkylamino, cycloalkylamino, arylamino, aralkylamino, alkyloxy, aryloxy or aralkyloxy; and provided that when (a) $A_1$ is Lys, $B_1$ is Ala, $C_1$ is Val, $D_1$ is Arg, $E_1$ is Ser, $F_1$ is Ser, $G_1$ is Asn, $H_1$ is Leu, $I_1$ is Val, $J_1$ is Pro and $K_1$ is Asn; or (b) $A_1$ is Lys, $B_1$ is Ala, $C_1$ is Val, $D_1$ is His, $E_1$ is Ser, $F_1$ is Asn, $G_1$ is Asn, $H_1$ is Leu, $I_1$ is Val, $J_1$ is Ser and $K_1$ is Asn;

then one or more of $A_1$ to $K_1$ is a D-amino acid and Z is selected from the group consisting of alkylamino, dialkylamino, cycloalkylamino, arylamino, aralkylamino, alkyloxy, aryloxy or aralkyloxy.

5. An agonist analogue of amylin according to claim 4 wherein X and Y are Cys residues linked by a disulfide bond.

6. An agonist analogue of amylin according to claim 5 wherein Z is amino.

7. An agonist analogue of amylin having the amino acid sequence:

$^1A_1-X-Asn-Thr-^5Ala-Thr-Y-Ala-Thr-^{10}Gln-Arg-$
$Leu-B_1-Asn-^{15}Phe-Leu-C_1-D_1-E_1-^{20}F_1-G_1-$
$Asn-H_1-Gly-^{25}I_1-J_1-Leu-Pro-Pro-^{30}Thr-K_1-$
$Val-Gly-Ser-^{35}Asn-Thr-Tyr-Z$ wherein $A_1$ is Lys, Ala, Ser or hydrogen;

$B_1$ is Ala, Ser or Thr;

$C_1$ is Val, Leu or Ile;

$D_1$ is His or Arg;

$E_1$ is Ser or Thr;

$F_1$ is Ser, Thr, Gln or Asn;

$G_1$ is Asn, Gln or His;

$H_1$ is Phe, Leu or Tyr;

$I_1$ is Ala or Pro;

$J_1$ is Ile, Val, Ala or Leu;

$K_1$ is Asn, Asp or Gln; X and Y are independently selected amino acid residues having side chains which are chemically bonded to each other to form an intramolecular linkage, wherein said intramolecular linkage is a disulfide bond, a lactam or a thioether linkage; and Z is amino, alkylamino, dialkylamino, cycloalkylamino, arylamino, aralkylamino, alkyloxy, aryloxy or aralkyloxy; and provided that when $A_1$ is Lys, $B_1$ is Ala, $C_1$ is Val, $D_1$ is Arg, $E_1$ is Ser, $F_1$ is Ser, $G_1$ is Asn, $H_1$ is Leu, $I_1$ is Pro, $J_1$ is Val and $K_1$ is Asn; then one or more of $A_1$ to $K_1$ is a D-amino acid and Z is selected from the group consisting of aralkylamino, dialkylamino, cycloalkylamino, arylamino, aralkylamino, alkyloxy, aryloxy or aralkyloxy.

8. An agonist analogue of amylin according to claim 7 wherein X and Y are Cys residues linked by a disulfide bond.

9. An agonist analogue of amylin according to claim 8 wherein Z is amino.

10. An agonist analogue of amylin having the amino acid sequence:

$^1A_1-X-Asn-Thr-^5Ala-Thr-Y-Ala-Thr-^{10}Gln-Arg-$
$Leu-B_1-Asn-^{15}Phe-Leu-C_1-D_1-E_1-^{20}F_1-G_1-$
$Asn-H_1-Gly-^{25}Pro-I_1-Leu-Pro-Pro-^{30}Thr-J_1-$
$Val-Gly-Ser-^{35}Asn-Thr-Tyr-Z$ wherein $A_1$ is Lys, Ala, Ser or hydrogen;

$B_1$ is Ala, Ser or Thr;

$C_1$ is Val, Leu or Ile;

$D_1$ is His or Arg;

$E_1$ is Ser or Thr;

$F_1$ is Ser, Thr, Gln or Asn;

$G_1$ is Asn, Gln or His;

$H_1$ is Phe, Leu or Tyr;

$I_1$ is Ile, Val, Ala or Leu;

$J_1$ is Asn, Asp or Gln; X and Y are independently selected amino acid residues having side chains which are chemically bonded to each other to form an intramolecular linkage wherein said intramolecular linkage is a disulfide bond, a lactam or a thioether linkage; and Z is amino, alkylamino, dialkylamino, cycloalkylamino, arylamino, aralkylamino, alkyloxy, aryloxy or aralkyloxy; and provided that when $A_1$ is Lys, $B_1$ is Ala, $C_1$ is Val, $D_1$ is Arg, $E_1$ is Ser, $F_1$ is Ser, $G_1$ is Asn, $H_1$ is Leu, $I_1$ is Val and $J_1$ is Asn; then one or more of $A_1$ to $K_1$ is a D-amino acid and Z is selected from the group consisting of alkylamino, dialkylamino, cycloalkylamino, arylamino, aralkylamino, alkyloxy, aryloxy or aralkyloxy.

11. An agonist analogue of amylin according to claim 10 wherein X and Y are Cys residues linked by a disulfide bond.

12. An agonist analogue of amylin according to claim 11 wherein Z is amino.

13. An agonist analogue of amylin according to any of claims 1–12 wherein $D_1$ is Arg.

14. An agonist analogue of amylin according to any of claims 1–6 or 10–12 wherein $I_1$ is Val.

15. An agonist analogue of amylin according to any of claims 7–9 where $J_1$ is Val.

16. An agonist analogue of amylin according to any of claims 1–12 wherein $A_1$ is hydrogen.

17. $^{18}$Arg$^{25,28}$Pro-h-amylin.

18. des-$^1$Lys$^{18}$Arg$^{25,28}$Pro-h-amylin.

19. $^{25,28,29}$Pro-h-amylin.

20. des-$^1$Lys$^{25,28,29}$Pro-h-amylin.

21. $^{18}$Arg$^{25,28,29}$Pro-h-amylin.

22. des-$^1$Lys$^{18}$Arg$^{25,28,29}$Pro-h-amylin.

23. $^{25}$Pro$^{26}$Val$^{28,29}$Pro-h-amylin.

24. An agonist analogue of amylin according to any of claims 1–16 which is an acetate salt.

25. An agonist analogue of amylin according to any of claims 1–16 which is a trifluoroacetate salt.

26. An agonist analogue of amylin according to any of claims 1–16 which is a hydrochloride salt.

27. A compound according to any of claims 17–23 which is an acetate salt.

28. A compound according to any of claims 17–23 which is a trifluoroacetate salt.

29. A compound according to any of claims 17–23 which is a hydrochloride salt.

30. A method for the treatment of diabetes mellitus in a mammal comprising the administration to said mammal of a therapeutically effective amount of an agonist analogue of amylin according to claim 3.

31. A method for the treatment of diabetes mellitus in a mammal comprising the administration to said mammal of a therapeutically effective amount of an agonist analogue of amylin according to claim 6.

32. A method for the treatment of diabetes mellitus in a mammal comprising the administration to said mammal of a therapeutically effective amount of an agonist analogue of amylin according to claim 9.

33. A method for the treatment of diabetes mellitus in a mammal comprising the administration to said mammal of a therapeutically effective amount of an agonist analogue of amylin according to claim 12.

34. A method for the treatment of diabetes mellitus in a mammal comprising the administration to said mammal of a therapeutically effective amount of an agonist analogue of amylin according to any of claims 17–23.

35. A method for the treatment of diabetes mellitus in a mammal comprising the administration to said mammal of a therapeutically effective amount of $^{25,28,29}$Pro-h-amylin.

36. The method of any of claims 30–35 further comprising the administration to said mammal of a therapeutically effective amount of an insulin.

37. A method for the treatment of diabetes mellitus in a mammal comprising the administration to said mammal of a therapeutically effective amount of $^{25,28,29}$Pro-h-amylin and a therapeutically effective amount of an insulin.

38. A composition comprising a therapeutically effective amount of an agonist analogue of amylin according to claim 3 in a pharmaceutically acceptable carrier.

39. A composition comprising a therapeutically effective amount of an agonist analogue of amylin according to claim 6 in a pharmaceutically acceptable carrier.

40. A composition comprising a therapeutically effective amount of an agonist analogue of amylin according to claim 9 in a pharmaceutically acceptable carrier.

41. A composition comprising a therapeutically effective amount of an agonist analogue of amylin according to claim 12 in a pharmaceutically acceptable carrier.

42. A composition comprising a therapeutically effective amount of an agonist analogue of amylin according to any of claims 17–23 in a pharmaceutically acceptable carrier.

43. A composition comprising a therapeutically effective amount of $^{25,28,29}$Pro-h-amylin in a pharmaceutically acceptable carrier.

44. A composition comprising a therapeutically effective amount of an agonist analogue of amylin according to any of claims 3, 6, 9, 11 and 17–23 and an insulin admixed in a pharmaceutically acceptable carrier.

45. A composition comprising a therapeutically effective amount of $^{25,28,29}$Pro-h-amylin and an insulin admixed in a pharmaceutically acceptable carrier.

* * * * *

UNITED STATES PATENT AND TRADEMARK OFFICE
CERTIFICATE OF CORRECTION

PATENT NO.   : 5,686,411
DATED        : November 11, 1997
INVENTOR(S)  : Gaeta et al.

It is certified that error appears in the above-identified patent and that said Letters Patent is hereby corrected as shown below:

Column 34,
Line 20, replace "aralkylamino" with -- alkylamino --; and
Line 56, replace "$K_1$" with -- $J_1$ --.

Signed and Sealed this

Seventh Day of October, 2003

JAMES E. ROGAN
*Director of the United States Patent and Trademark Office*

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO: 1:

```
Lys Cys Asn Thr Ala Thr Cys Ala Thr Gln Arg Leu Ala Asn Phe
1               5                   10                  15
Leu Val His Ser Ser Asn Asn Phe Gly Ala Ile Leu Pro Ser Thr
                20                  25                  30
Asn Val Gly Ser Asn Thr Tyr
                35
```

( 2 ) INFORMATION FOR SEQ ID NO:2:

( i ) SEQUENCE CHARACTERISTICS:
        ( A ) LENGTH: 37 amino acids
        ( B ) TYPE: amino acids
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Lys Cys Asn Thr Ala Thr Cys Ala Thr Gln Arg Leu Ala Asn Phe
1               5                   10                  15
Leu Val His Ser Ser Asn Asn Phe Gly Pro Val Leu Pro Pro Thr
                20                  25                  30
Asn Val Gly Ser Asn Thr Tyr
                35
```

( 2 ) INFORMATION FOR SEQ ID NO:3:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Lys Asp Asn Thr Ala Thr Lys Ala Thr Gln Arg Leu Ala Asn Phe
1               5                   10                  15
Leu Val His Ser Ser Asn Asn Phe Gly Ala Ile Leu Ser Ser Thr
                20                  25                  30
Asn Val Gly Ser Asn Thr Tyr
                35
```

( 2 ) INFORMATION FOR SEQ ID NO:4:

( i ) SEQUENCE CHARACTERISTICS:
        ( A ) LENGTH: 36 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:4:

| Cys | Asn | Thr | Ala | Thr | Cys | Ala | Thr | Gln | Arg | Leu | Ala | Asn | Phe | Leu |
|---|---|---|---|---|---|---|---|---|---|---|---|---|---|---|
| 1 | | | | 5 | | | | | 10 | | | | | 15 |

| Val | His | Ser | Ser | Asn | Asn | Phe | Gly | Ala | Ile | Leu | Ser | Ser | Thr | Asn |
|---|---|---|---|---|---|---|---|---|---|---|---|---|---|---|
| | | | | 20 | | | | | 25 | | | | | 30 |

| Val | Gly | Ser | Asn | Thr | Tyr |
|---|---|---|---|---|---|
| | | | | 35 | |

(2) INFORMATION FOR SEQ ID NO:5:

(i) SEQUENCE CHARACTERISTICS:
    (A) LENGTH: 37 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:5:

| Ala | Cys | Asn | Thr | Ala | Thr | Cys | Ala | Thr | Gln | Arg | Leu | Ala | Asn | Phe | Leu |
|---|---|---|---|---|---|---|---|---|---|---|---|---|---|---|---|
| 1 | | | | 5 | | | | | 10 | | | | | | 15 |

| Val | His | Ser | Ser | Asn | Asn | Phe | Gly | Ala | Ile | Leu | Ser | Ser | Thr | Asn | Val |
|---|---|---|---|---|---|---|---|---|---|---|---|---|---|---|---|
| | | | 20 | | | | | 25 | | | | | 30 | | |

| Gly | Ser | Asn | Thr | Tyr |
|---|---|---|---|---|
| | | | 35 | |

(2) INFORMATION FOR SEQ ID NO:6:

(i) SEQUENCE CHARACTERISTICS:
    (A) LENGTH: 37 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:6:

| Ser | Cys | Asn | Thr | Ala | Thr | Cys | Ala | Thr | Gln | Arg | Leu | Ala | Asn | Phe |
|---|---|---|---|---|---|---|---|---|---|---|---|---|---|---|
| 1 | | | | 5 | | | | | 10 | | | | | 15 |

| Leu | Val | His | Ser | Ser | Asn | Asn | Phe | Gly | Ala | Ile | Leu | Ser | Ser | Thr |
|---|---|---|---|---|---|---|---|---|---|---|---|---|---|---|
| | | | | 20 | | | | | 25 | | | | | 30 |

| Asn | Val | Gly | Ser | Asn | Thr | Tyr |
|---|---|---|---|---|---|---|
| | | | | 35 | | |

(2) INFORMATION FOR SEQ ID NO:7:

(i) SEQUENCE CHARACTERISTICS:
    (A) LENGTH: 37 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:7:

| Lys | Cys | Asn | Thr | Ala | Thr | Cys | Ala | Thr | Gln | Arg | Leu | Ala | Asn | Phe |
|---|---|---|---|---|---|---|---|---|---|---|---|---|---|---|
| 1 | | | | 5 | | | | | 10 | | | | | 15 |

| Leu | Val | His | Ser | Ser | Asn | Asn | Phe | Gly | Ala | Ile | Leu | Ser | Pro | Thr |
|---|---|---|---|---|---|---|---|---|---|---|---|---|---|---|
| | | | | 20 | | | | | 25 | | | | | 30 |

| Asn | Val | Gly | Ser | Asn | Thr | Tyr |
|---|---|---|---|---|---|---|
| | | | | 35 | | |

( 2 ) INFORMATION FOR SEQ ID NO:8:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Lys Cys Asn Thr Ala Thr Cys Ala Thr Gln Arg Leu Ala Asn Phe
1               5                   10                  15

Leu Val His Ser Ser Asn Asn Phe Gly Pro Ile Leu Pro Ser Thr
                20                  25                  30

Asn Val Gly Ser Asn Thr Tyr
                35
```

( 2 ) INFORMATION FOR SEQ ID NO:9:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Ser Thr Asn
                20                  25                  30

Val Gly Ser Asn Thr Tyr
                35
```

( 2 ) INFORMATION FOR SEQ ID NO:10:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Lys Cys Asn Thr Ala Thr Cys Ala Thr Gln Arg Leu Ala Asn Phe
1               5                   10                  15

Leu Val Arg Ser Ser Asn Asn Phe Gly Pro Ile Leu Pro Ser Thr
                20                  25                  30

Asn Val Gly Ser Asn Thr Tyr
                35
```

( 2 ) INFORMATION FOR SEQ ID NO:11:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Cys Asn Thr Ala Thr Cys Ala Thr Gln Arg Leu Arg Asn Phe Leu
1               5                   10                  15

Val His Ser Ser Asn Asn Phe Gly Pro Ile Leu Pro Ser Thr Asn
                20                  25                  30

Val Gly Ser Asn Thr Tyr
                35
```

( 2 ) INFORMATION FOR SEQ ID NO:12:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Lys Cys Asn Thr Ala Thr Cys Ala Thr Gln Arg Leu Ala Asn Phe
1               5                   10                  15

Leu Val Arg Ser Ser Asn Asn Phe Gly Pro Ile Leu Pro Pro Thr
                20                  25                  30

Asn Val Gly Ser Asn Thr Tyr
                35
```

( 2 ) INFORMATION FOR SEQ ID NO:13:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Pro Thr Asn
                20                  25                  30

Val Gly Ser Asn Thr Tyr
                35
```

( 2 ) INFORMATION FOR SEQ ID NO:14:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
                20                  25                  30

Gly Ser Asn Thr Tyr
                35
```

( 2 ) INFORMATION FOR SEQ ID NO:15:

( i ) SEQUENCE CHARACTERISTICS:
        ( A ) LENGTH: 36 amino acids ( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:15:

```
Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn
                20                  25                  30

Val Gly Ser Asn Thr Tyr
                35
```

( 2 ) INFORMATION FOR SEQ ID NO:16:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:16:

```
Lys Ala Val His Ser Ser Asn Leu Pro Val Pro Pro Asn
1               5                   10
```

( 2 ) INFORMATION FOR SEQ ID NO:17:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:17:

```
Lys Ala Val His Ser Ser Asn Leu Pro Val Pro Ser Asn
1               5                   10
```

( 2 ) INFORMATION FOR SEQ ID NO:18:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptides ( x i ) SEQUENCE DESCRIPTION: SEQ ID NO:18:

```
Ala Val His Ser Ser Asn Leu Pro Val Pro Ser Asn
1               5                   10
```

( 2 ) INFORMATION FOR SEQ ID NO:19:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:19:

```
Lys Ala Val Arg Ser Ser Asn Leu Pro Val Pro Ser Asn
1               5                   10
```

( 2 ) INFORMATION FOR SEQ ID NO:20:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Lys Ala Val Arg Ser Ser Asn Leu Pro Ile Pro Pro Asn
1               5                   10

( 2 ) INFORMATION FOR SEQ ID NO:21:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

Lys Ala Val Arg Ser Ser Asn Leu Pro Ile Pro Ser Asn
1               5                   10

( 2 ) INFORMATION FOR SEQ ID NO:22:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

Lys Ala Ile His Ser Ser Asn Leu Pro Ile Pro Pro Asn
1               5                   10

( 2 ) INFORMATION FOR SEQ ID NO:23:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

Lys Ala Ile His Ser Ser Asn Phe Pro Ile Pro Pro Asn
1               5                   10

( 2 ) INFORMATION FOR SEQ ID NO:24:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

Ala Ile His Ser Ser Asn Leu Pro Ile Pro Pro Asn
1               5                   10

( 2 ) INFORMATION FOR SEQ ID NO:25:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

```
Lys Ala Ile Arg Ser Ser Asn Leu Ala Ile Ser Ser Asn
1               5                   10
```

( 2 ) INFORMATION FOR SEQ ID NO:26:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

```
Lys Ala Ile Arg Ser Ser Asn Leu Ala Val Ser Pro Asn
1               5                   10
```

( 2 ) INFORMATION FOR SEQ ID NO:27:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

```
Lys Ala Ile Arg Ser Ser Asn Leu Pro Val Pro Pro Asn
1               5                   10
```

( 2 ) INFORMATION FOR SEQ ID NO:28:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

```
Lys Thr Val His Ser Ser His Leu Ala Ala Leu Pro Asp
1               5                   10
```

( 2 ) INFORMATION FOR SEQ ID NO:29:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:29:

```
Lys Thr Val His Ser Ser His Leu Ala Ala Ser Pro Asp
1               5                   10
```

( 2 ) INFORMATION FOR SEQ ID NO:30:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:30:

Thr Val His Ser Ser His Leu Ala Ala Pro Ser Asp
 1           5                   10

( 2 ) INFORMATION FOR SEQ ID NO:31:

( i ) SEQUENCE CHARACTERISTICS:
      ( A ) LENGTH: 13 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:31:

Lys Thr Val Arg Ser Ser His Leu Ala Ala Ser Pro Asp
 1           5                   10

( 2 ) INFORMATION FOR SEQ ID NO:32:

( i ) SEQUENCE CHARACTERISTICS:
      ( A ) LENGTH: 13 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:32:

Lys Thr Val Arg Ser Ser His Leu Ala Ile Pro Pro Asp
 1           5                   10

( 2 ) INFORMATION FOR SEQ ID NO:33:

( i ) SEQUENCE CHARACTERISTICS:
      ( A ) LENGTH: 13 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:33:

Lys Thr Val Arg Ser Ser His Leu Pro Ala Pro Pro Asp
 1           5                   10